(12) United States Patent
Angel et al.

(10) Patent No.: US 10,376,685 B2
(45) Date of Patent: Aug. 13, 2019

(54) THROMBUS DETECTION DEVICE AND METHOD

(71) Applicant: BIO2 MEDICAL, INC., Golden, CO (US)

(72) Inventors: Luis F. Angel, San Antonio, TX (US); Rogelio I. Guerra, Denver, CO (US)

(73) Assignee: Mermaid Medical Vascular ApS, Stenlose (DK)

( * ) Notice: Subject to any disclaimer, the term of this patent is extended or adjusted under 35 U.S.C. 154(b) by 328 days.

(21) Appl. No.: 15/136,636

(22) Filed: Apr. 22, 2016

(65) Prior Publication Data

US 2016/0317163 A1    Nov. 3, 2016

Related U.S. Application Data

(60) Provisional application No. 62/151,812, filed on Apr. 23, 2015.

(51) Int. Cl.
*A61F 2/01* (2006.01)
*A61M 1/00* (2006.01)
(Continued)

(52) U.S. Cl.
CPC ..... *A61M 39/10* (2013.01); *A61B 2017/2212* (2013.01); *A61B 2017/22079* (2013.01);
(Continued)

(58) Field of Classification Search
CPC ...... A61F 2/013; A61F 2/01; A61F 2002/011; A61F 2002/015; A61F 2002/016;
(Continued)

(56) References Cited

U.S. PATENT DOCUMENTS 3,671,979 A    6/1972  Moulopoulos ................. 3/1
4,901,731 A    2/1990  Millar ......................... 128/675
(Continued)

FOREIGN PATENT DOCUMENTS

WO    WO 1996/030073    10/1996    ............ A61M 29/00
WO    WO 1997/017100     5/1997    ............ A61M 29/00
(Continued)

OTHER PUBLICATIONS

Decousus, et al., "A clinical trial of vena caval filters in the prevention of pulmonary embolism in patients with proximal deep-vein thrombosis" *N Engl J Med* 338(7): 409-415 (1998).
(Continued)

*Primary Examiner* — Katrina M Stransky
(74) *Attorney, Agent, or Firm* — David G. Rosenbaum; Benjamin D. Rotman; Rosenbaum IP, P.C.

(57) ABSTRACT

A thrombus detection device comprising an elongate tube having at least one opening at a distal end of the elongate tube. A coupling is attached or formed at the proximal end of the elongate tube. The detection of the presence of a thrombus is performed by using a syringe to withdraw blood through the at least one thrombus detection opening at the distal end of the elongate tube. If little or no blood is withdrawn, or if the withdrawal of blood is more difficult than expected, the presence of a thrombus obstructing the openings is indicated.

6 Claims, 5 Drawing Sheets

(51) Int. Cl.
*A61B 17/22* (2006.01)
*A61B 90/00* (2016.01)
*A61M 39/10* (2006.01)
*A61B 17/221* (2006.01)

(52) U.S. Cl.
CPC . *A61B 2090/063* (2016.02); *A61B 2090/0807* (2016.02); *A61F 2/013* (2013.01); *A61M 1/0068* (2014.02)

(58) Field of Classification Search
CPC ......... A61F 2002/018; A61B 17/22031; A61B 2017/22079; A61B 17/221; A61M 39/10; A61M 1/0068
See application file for complete search history.

(56) References Cited

U.S. PATENT DOCUMENTS

| | | | |
|---|---|---|---|
| 4,921,479 A | 5/1990 | Grayzel | 604/53 |
| 4,969,891 A | 11/1990 | Gerwertz | 606/200 |
| 5,046,503 A | 9/1991 | Schneiderman | 128/692 |
| 5,053,008 A | 10/1991 | Bajaj | 604/104 |
| 5,102,415 A * | 4/1992 | Guenther | A61B 17/22 604/103.05 |
| 5,112,347 A | 5/1992 | Taheri | 606/200 |
| 5,163,928 A | 11/1992 | Hobbs et al. | 604/281 |
| 5,201,757 A | 4/1993 | Heyn et al. | 606/200 |
| 5,549,626 A | 8/1996 | Miller et al. | 606/200 |
| 5,569,215 A | 10/1996 | Crocker | 604/264 |
| 5,624,596 A | 4/1997 | McNamara et al. | 604/93 |
| 5,707,389 A | 1/1998 | Louw et al. | 606/200 |
| 5,713,917 A | 2/1998 | Leonhardt et al. | 606/194 |
| 5,715,829 A | 2/1998 | Cori et al. | 128/673 |
| 5,766,151 A | 6/1998 | Valley et al. | 604/96 |
| 5,769,816 A | 6/1998 | Barbut et al. | 604/96 |
| 5,791,341 A | 8/1998 | Bullard | 128/207.15 |
| 5,795,322 A | 8/1998 | Boudewijn | 604/22 |
| 5,795,325 A | 8/1998 | Valley et al. | 604/53 |
| 5,797,920 A | 8/1998 | Kim | 606/108 |
| 5,814,064 A | 9/1998 | Daniel et al. | 606/200 |
| 5,833,650 A | 11/1998 | Imran | 604/53 |
| 5,848,964 A | 12/1998 | Samuels | 600/200 |
| 5,879,499 A | 3/1999 | Corvi | 156/175 |
| 5,893,868 A | 4/1999 | Hanson et al. | 606/198 |
| 5,925,016 A | 7/1999 | Chornenky et al. | 604/96 |
| 5,947,994 A | 9/1999 | Louw et al. | 606/200 |
| 5,947,995 A | 9/1999 | Samuels | 606/200 |
| 5,954,742 A | 9/1999 | Osypka | 606/198 |
| 5,976,172 A | 11/1999 | Homsma et al. | 606/200 |
| 5,980,478 A | 11/1999 | Gorsuch et al. | 604/4 |
| 5,980,555 A | 11/1999 | Barbut et al. | 600/200 |
| 5,989,281 A | 11/1999 | Barbut et al. | 606/200 |
| 6,007,544 A | 12/1999 | Kim | 606/108 |
| 6,036,654 A | 3/2000 | Quinn et al. | 600/526 |
| 6,051,014 A | 4/2000 | Jang | 606/200 |
| 6,086,605 A | 7/2000 | Barbut et al. | 606/200 |
| 6,090,097 A | 7/2000 | Barbut et al. | 604/511 |
| 6,117,154 A | 9/2000 | Barbut et al. | 606/181 |
| 6,135,991 A | 10/2000 | Muni et al. | 604/509 |
| 6,136,016 A | 10/2000 | Barbut et al. | 606/200 |
| 6,152,909 A | 11/2000 | Bagaoisan et al. | 604/523 |
| 6,165,179 A | 12/2000 | Cathcart et al. | 606/108 |
| 6,171,328 B1 | 1/2001 | Addis | 606/200 |
| 6,178,968 B1 | 1/2001 | Louw et al. | 128/898 |
| 6,231,544 B1 | 3/2001 | Tsugita et al. | 604/104 |
| 6,224,627 B1 | 5/2001 | Armstrong et al. | 623/1.23 |
| 6,235,045 B1 | 5/2001 | Barbut et al. | 606/200 |
| 6,251,093 B1 | 6/2001 | Valley et al. | 604/96 |
| 6,270,477 B1 | 8/2001 | Bagaoisan et al. | 604/96.01 |
| 6,277,138 B1 | 8/2001 | Levinson et al. | 606/200 |
| 6,287,321 B1 | 9/2001 | Jang | 606/200 |
| 6,315,792 B1 | 11/2001 | Armstrong et al. | 623/1.13 |
| 6,336,934 B1 | 1/2002 | Gilson et al. | 606/200 |
| 6,344,049 B1 | 2/2002 | Levinson et al. | 606/200 |
| 6,344,053 B1 | 2/2002 | Boneau | 623/1.11 |
| 6,361,545 B1 | 3/2002 | Macoviak et al. | 606/200 |
| 6,379,373 B1 | 4/2002 | Sawhney et al. | 606/193 |
| 6,383,196 B1 | 5/2002 | Leslie et al. | 606/114 |
| 6,423,086 B1 | 7/2002 | Barbut et al. | 606/200 |
| 6,432,122 B1 | 8/2002 | Gilson et al. | 606/200 |
| 6,443,971 B1 | 9/2002 | Boylan et al. | 606/200 |
| 6,454,741 B1 | 9/2002 | Muni et al. | 604/96.01 |
| 6,468,291 B2 | 10/2002 | Bates et al. | 606/200 |
| 6,482,171 B1 | 11/2002 | Corvi et al. | 604/96.01 |
| 6,511,503 B1 | 1/2003 | Burkett et al. | 623/1.11 |
| 6,537,294 B1 | 3/2003 | Boyle et al. | 606/200 |
| 6,537,296 B2 | 3/2003 | Levinson et al. | 606/200 |
| 6,537,297 B2 | 3/2003 | Tsugita et al. | 606/200 |
| 6,544,279 B1 | 4/2003 | Hopkins et al. | 606/200 |
| 6,547,788 B1 | 4/2003 | Maguire et al. | 604/41 |
| 6,561,996 B1 | 5/2003 | Gorsuch | 604/6.09 |
| 6,569,148 B2 | 5/2003 | Bagaoisan et al. | 604/509 |
| 6,585,639 B1 | 7/2003 | Kotmel et al. | 600/116 |
| 6,589,264 B1 | 7/2003 | Barbut et al. | 606/200 |
| 6,592,546 B1 | 7/2003 | Barbut et al. | 604/96.01 |
| 6,596,011 B2 | 7/2003 | Johnson et al. | 606/200 |
| 6,616,680 B1 | 9/2003 | Theilen | 606/200 |
| 6,623,507 B2 | 9/2003 | Saleh | 606/200 |
| 6,635,070 B2 | 10/2003 | Leeflang et al. | 606/200 |
| 6,669,708 B1 | 12/2003 | Nissenbaum et al. | 606/153 |
| 6,685,722 B1 | 2/2004 | Rosenbluth et al. | 606/200 |
| 6,689,148 B2 | 2/2004 | Sawhney et al. | 606/193 |
| 6,692,512 B2 | 2/2004 | Jang | 606/200 |
| 6,726,651 B1 | 4/2004 | Robinson et al. | 604/101.01 |
| 6,726,702 B2 | 4/2004 | Khosravi | 606/200 |
| 6,749,619 B2 | 6/2004 | Ouriel et al. | 606/200 |
| 6,755,813 B2 | 6/2004 | Ouriel et al. | 604/537 |
| 6,780,193 B2 | 8/2004 | Leslie et al. | 606/114 |
| 6,805,692 B2 | 10/2004 | Muni et al. | 604/509 |
| 6,869,431 B2 | 3/2005 | Maguire et al. | 604/41 |
| 6,885,115 B2 | 4/2005 | Hatori et al. | 307/80 |
| 6,887,257 B2 | 5/2005 | Salahieh et al. | 606/200 |
| 6,913,600 B2 | 7/2005 | Valley et al. | 604/509 |
| 6,986,778 B2 | 1/2006 | Zadno-Azizi | 606/200 |
| 7,011,672 B2 | 3/2006 | Barbut et al. | 606/200 |
| 7,060,082 B2 | 6/2006 | Goll et al. | 606/200 |
| 7,108,708 B2 | 9/2006 | Cheng et al. | 606/200 |
| 7,125,414 B2 | 10/2006 | Blackledge et al. | 606/200 |
| 7,144,408 B2 | 12/2006 | Keegan et al. | 606/200 |
| 7,150,737 B2 | 12/2006 | Purdy et al. | 604/506 |
| 7,153,320 B2 | 12/2006 | Euteneuer et al. | 606/200 |
| 7,163,520 B2 | 1/2007 | Bernard et al. | 604/6.9 |
| 7,166,570 B2 | 1/2007 | Hunter et al. | 514/2 |
| 7,220,270 B2 | 5/2007 | Sawhney et al. | 606/193 |
| 7,261,727 B2 | 8/2007 | Thielen | 606/200 |
| 7,544,202 B2 | 6/2009 | Cartier et al. | 606/200 |
| 7,985,236 B2 | 7/2011 | Pepper | 606/194 |
| 8,231,519 B2 | 7/2012 | Reichenbach et al. | 600/16 |
| 2001/0001812 A1 | 5/2001 | Valley et al. | 604/96.01 |
| 2001/0031981 A1 | 10/2001 | Evan et al. | 606/200 |
| 2002/0062134 A1 | 5/2002 | Barbut et al. | 606/200 |
| 2002/0072730 A1 | 6/2002 | McGill et al. | 604/525 |
| 2002/0082525 A1 | 6/2002 | Oslund et al. | 600/585 |
| 2002/0082636 A1 | 6/2002 | Sawhney et al. | 606/193 |
| 2002/0091407 A1 | 7/2002 | Zadno-Azizi et al. | 606/200 |
| 2002/0107479 A1 | 8/2002 | Bates et al. | 604/96.01 |
| 2002/0107503 A1 | 8/2002 | McGuckin, Jr. et al. | 604/523 |
| 2002/0115983 A1 | 8/2002 | Sekino et al. | 604/528 |
| 2002/0165575 A1 | 11/2002 | Saleh | 606/200 |
| 2002/0188313 A1 | 12/2002 | Johnson et al. | 606/200 |
| 2003/0009146 A1 | 1/2003 | Muni et al. | 604/500 |
| 2003/0032941 A1 | 2/2003 | Boyle et al. | 604/533 |
| 2003/0050600 A1 | 3/2003 | Reesemann et al. | 604/101.01 |
| 2003/0093110 A1 | 5/2003 | Vale | 606/200 |
| 2003/0097082 A1 | 5/2003 | Purdy et al. | 606/594 |
| 2003/0097094 A1 | 5/2003 | Ouriel et al. | 604/93.01 |
| 2003/0125764 A1 | 7/2003 | Brady et al. | 606/200 |
| 2003/0144686 A1 | 7/2003 | Martinez et al. | 606/200 |
| 2003/0176889 A1 | 9/2003 | Boyle et al. | 606/200 |
| 2003/0187495 A1 | 10/2003 | Cully et al. | 623/1.15 |
| 2003/0203031 A1 | 10/2003 | Shah | 424/485 |
| 2003/0208222 A1 | 11/2003 | Zadno-Azizi | 606/194 |
| 2003/0212429 A1 | 11/2003 | Keegan et al. | 606/200 |
| 2003/0212434 A1 | 11/2003 | Thielen | 606/200 |

(56) References Cited

U.S. PATENT DOCUMENTS

| | | | |
|---|---|---|---|
| 2003/0233117 A1 | 12/2003 | Adams et al. | 606/200 |
| 2004/0006367 A1 | 1/2004 | Johnson et al. | 606/200 |
| 2004/0011740 A1 | 1/2004 | Bernard et al. | 210/646 |
| 2004/0044302 A1 | 3/2004 | Bernard et al. | 604/6.09 |
| 2004/0102806 A1 | 5/2004 | Broome et al. | 606/200 |
| 2004/0125764 A1 | 7/2004 | Brady et al. | 606/200 |
| 2004/0153112 A1 | 8/2004 | Nissenbaum et al. | 606/185 |
| 2004/0158276 A1 | 8/2004 | Barbut et al. | 606/200 |
| 2004/0162576 A1 | 8/2004 | Barbut et al. | 606/200 |
| 2004/0199177 A1 | 10/2004 | Kim | 606/108 |
| 2004/0220612 A1 | 11/2004 | Swainston et al. | 606/200 |
| 2004/0236170 A1 | 11/2004 | Kim | 600/16 |
| 2004/0254528 A1 | 12/2004 | Adams et al. | 604/96.01 |
| 2005/0021075 A1 | 1/2005 | Bonnette et al. | 606/200 |
| 2005/0027236 A1 | 2/2005 | Douk et al. | 604/40 |
| 2005/0038468 A1 | 2/2005 | Panetta et al. | 606/200 |
| 2005/0038503 A1 | 2/2005 | Greenhalgh et al. | 623/1.42 |
| 2005/0080445 A1 | 4/2005 | Sawhney et al. | 606/193 |
| 2005/0085769 A1 | 4/2005 | MacMahon et al. | 604/96.01 |
| 2005/0085841 A1 | 4/2005 | Eversull et al. | 606/190 |
| 2005/0107817 A1 | 5/2005 | White et al. | 606/191 |
| 2005/0113862 A1 | 5/2005 | Besselink et al. | 606/200 |
| 2005/0133046 A1 | 6/2005 | Becker et al. | 128/898 |
| 2005/0142163 A1 | 6/2005 | Hunter et al. | 424/423 |
| 2005/0145258 A1 | 7/2005 | Dong | 128/898 |
| 2005/0147562 A1 | 7/2005 | Hunter et al. | 424/9.5 |
| 2005/0147599 A1 | 7/2005 | Hunter et al. | 424/94.63 |
| 2005/0147643 A1 | 7/2005 | Hunter et al. | 424/423 |
| 2005/0148512 A1 | 7/2005 | Hunter et al. | 514/12 |
| 2005/0148997 A1 | 7/2005 | Valley et al. | 604/509 |
| 2005/0158274 A1 | 7/2005 | Hunter et al. | 424/78.38 |
| 2005/0169958 A1 | 8/2005 | Hunter et al. | 424/423 |
| 2005/0169959 A1 | 8/2005 | Hunter et al. | 424/423 |
| 2005/0175657 A1 | 8/2005 | Hunter et al. | 424/422 |
| 2005/0177186 A1 | 8/2005 | Cully et al. | 606/200 |
| 2005/0186247 A1 | 8/2005 | Hunter et al. | 424/423 |
| 2005/0191248 A1 | 9/2005 | Hunter et al. | 424/50 |
| 2005/0192620 A1 | 9/2005 | Cully et al. | 606/200 |
| 2005/0197624 A1 | 9/2005 | Goodson, IV et al. | 604/96.01 |
| 2005/0205097 A1 | 9/2005 | Kyle, Jr. | 128/207.14 |
| 2005/0245962 A1 | 11/2005 | Adams et al. | 606/194 |
| 2005/0261733 A1 | 11/2005 | Cheng et al. | 606/200 |
| 2005/0267408 A1 | 12/2005 | Grandt et al. | 604/103.04 |
| 2005/0267442 A1 | 12/2005 | Von Oepen | 604/509 |
| 2005/0277976 A1 | 12/2005 | Galdonik et al. | 606/200 |
| 2005/0283182 A1 | 12/2005 | Pierce et al. | 606/200 |
| 2006/0025840 A1 | 2/2006 | Willard | 607/113 |
| 2006/0135961 A1 | 6/2006 | Rosenman et al. | 606/108 |
| 2006/0189921 A1 | 8/2006 | Galdonik et al. | 604/27 |
| 2006/0190025 A1 | 8/2006 | Lehe et al. | 606/200 |
| 2006/0200191 A1 | 9/2006 | Zadno-Azizi | 606/200 |
| 2006/0229657 A1 | 10/2006 | Wasicek et al. | 606/200 |
| 2006/0240063 A9 | 10/2006 | Hunter et al. | 424/423 |
| 2006/0240064 A9 | 10/2006 | Hunter et al. | 424/423 |
| 2006/0241675 A1 | 10/2006 | Johnson et al. | 606/200 |
| 2006/0241676 A1 | 10/2006 | Johnson et al. | 606/200 |
| 2006/0241677 A1 | 10/2006 | Johnson et al. | 606/200 |
| 2006/0241678 A1 | 10/2006 | Johnson et al. | 606/200 |
| 2006/0241679 A1 | 10/2006 | Johnson et al. | 606/200 |
| 2006/0241680 A1 | 10/2006 | Johnson et al. | 606/200 |
| 2006/0248871 A1 | 11/2006 | Johnson et al. | 57/58.83 |
| 2006/0271098 A1 | 11/2006 | Peacock, III | 606/200 |
| 2007/0006441 A1 | 1/2007 | McNiven et al. | 29/508 |
| 2007/0016132 A1 | 1/2007 | Oepen et al. | 604/96.01 |
| 2007/0016165 A1 | 1/2007 | Von Oepen et al. | 604/525 |
| 2007/0021771 A1 | 1/2007 | Oepen et al. | 606/194 |
| 2007/0055365 A1 | 3/2007 | Greenberg et al. | 623/1.44 |
| 2007/0060942 A2 | 3/2007 | Zadno-Azizi | 606/194 |
| 2007/0065484 A1 | 3/2007 | Chudzik et al. | 424/426 |
| 2007/0083188 A1 | 4/2007 | Grandt et al. | 604/524 |
| 2007/0123838 A1 | 5/2007 | Bernard et al. | 604/500 |
| 2007/0129752 A1 | 6/2007 | Webler et al. | 606/200 |
| 2007/0129753 A1 | 6/2007 | Quinn et al. | 606/200 |
| 2007/0135832 A1* | 6/2007 | Wholey | A61F 2/013 606/200 |
| 2007/0191717 A1 | 8/2007 | Rosen et al. | 600/485 |
| 2007/0204455 A1 | 9/2007 | Knott et al. | 29/508 |
| 2007/0208374 A1 | 9/2007 | Boyle et al. | 606/200 |
| 2007/0244503 A1 | 10/2007 | Casey et al. | 606/200 |
| 2007/0293930 A1 | 12/2007 | Wang et al. | 623/1.11 |
| 2008/0051671 A1 | 2/2008 | Broome et al. | 600/504 |
| 2009/0043332 A1 | 2/2009 | Sullivan et al. | 606/200 |
| 2009/0062480 A1 | 3/2009 | Angel | 606/200 |
| 2010/0137892 A1 | 6/2010 | Krolik et al. | 606/159 |
| 2011/0190727 A1 | 8/2011 | Edmunds et al. | 604/509 |
| 2012/0158039 A1 | 6/2012 | Angel et al. | 606/200 |

FOREIGN PATENT DOCUMENTS

| | | | |
|---|---|---|---|
| WO | WO 1997/042879 | 11/1997 | A61B 17/00 |
| WO | WO 1998/046297 | 10/1998 | A61M 29/00 |
| WO | WO 1999/065420 | 12/1999 | A61F 2/06 |
| WO | WO 2000/009190 | 2/2000 | A61M 25/00 |
| WO | WO 2001/013983 | 3/2001 | A61M 25/00 |
| WO | WO 2001/037921 | 5/2001 | A61M 29/00 |
| WO | WO 2001/052768 | 7/2001 | A61F 2/01 |
| WO | WO 2001/065936 | 9/2001 | C12N 11/04 |
| WO | WO 2002/030271 | 4/2002 | |
| WO | WO 2002/039878 | 5/2002 | |
| WO | WO 2002/040090 | 5/2002 | A61M 29/00 |
| WO | WO 2002/064202 | 8/2002 | A61M 25/00 |
| WO | WO 2003/015859 | 2/2003 | A61M 25/06 |
| WO | WO 2003/084437 | 10/2003 | |
| WO | WO 2004/014240 | 2/2004 | A61B 17/12 |
| WO | WO 2004/049932 | 6/2004 | A61B 5/0215 |
| WO | WO 2004/054650 | 7/2004 | A61M 25/00 |
| WO | WO 2004/060465 | 7/2004 | A61M 25/06 |
| WO | WO 2004/098674 | 11/2004 | A61M 2/03 |
| WO | WO 2005/011786 | 2/2005 | A61M 25/00 |
| WO | WO 2005/023358 | 3/2005 | A61M 25/00 |
| WO | WO 2005/046746 | 5/2005 | A61B 17/11 |
| WO | WO 2005/058384 | 6/2005 | A61L 29/00 |
| WO | WO 2005/065079 | 7/2005 | A61F 2/02 |
| WO | WO 2005/074520 | 8/2005 | |
| WO | WO 2005/091910 | 10/2005 | |
| WO | WO 2005/118044 | 12/2005 | A61M 25/00 |
| WO | WO 2005/118045 | 12/2005 | A61M 25/00 |
| WO | WO 2005/118050 | 12/2005 | A61M 29/00 |
| WO | WO 2006/065949 | 6/2006 | A61F 11/10 |
| WO | WO 2006/074163 | 7/2006 | B01D 71/06 |
| WO | WO 2006/089178 | 8/2006 | A61M 25/00 |
| WO | WO 2006/104591 | 10/2006 | A61M 25/00 |
| WO | WO 2006/105065 | 10/2006 | A61F 2/01 |
| WO | WO 2006/116636 | 11/2006 | A61F 2/06 |
| WO | WO 2006/127929 | 11/2006 | A61M 29/00 |
| WO | WO 2007/035865 | 3/2007 | A61M 27/00 |
| WO | WO 2007/035885 | 3/2007 | A61L 21/20 |

OTHER PUBLICATIONS

Extended Search Report from corresponding application, EP 08799012.3, pp. 1-7 (dated Jun. 6, 2011).

Extended Search Report from corresponding application, EP 11732246.1, pp. 1-9 (dated Jun. 2, 2016).

Greenfield, L., et al., "A new intracaval filter permitting continued flow and resolution of emboli" *Surgery* 73(4): 599-606 (1973).

Lin, et al., "Vena caval filters in the treatment of acute DVT" *Endovascular Today* Jan: 40-50 (2005).

Mobin-Uddin, et al., "experimental prevention of myocardial infarction by bronchial collateral circulation" *JAMA* 208(2): 301-306 (1969).

International Preliminary Report on Patentability from corresponding PCT international application PCT/US2014/017170, pp. 1-14 (dated Sep. 17, 2015).

PCT International Search Report from corresponding PCT international application PCT/US2008/074885, pp. 1-3 (dated Nov. 26, 2008).

PCT International Search Report from corresponding PCT international application PCT/US2011/020599, pp. 1-7 (dated Oct. 31, 2011).

PCT Written Opinion from corresponding PCT international application PCT/US2008/074885, pp. 1-8 (dated Nov. 26, 2008).

(56) References Cited

OTHER PUBLICATIONS

PCT Written Opinion from corresponding PCT international application PCT/US2011/020599, pp. 1-5 (dated Oct. 31, 2011).

* cited by examiner

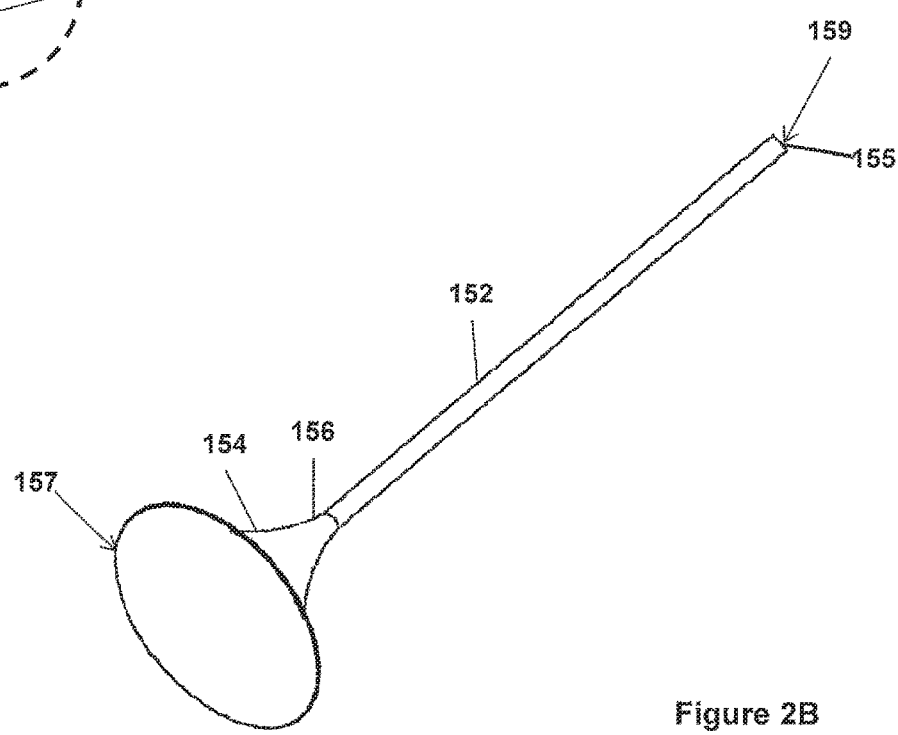
Figure 2B
AMENDED

THROMBUS DETECTION DEVICE AND METHOD

CROSS-REFERENCE TO RELATED APPLICATIONS

This application claims the benefit of priority to U.S. Provisional Patent Application Ser. No. 62/151,812 filed Apr. 23, 2015, which is herein incorporated by reference in its entirety. This Application is related to commonly owned and co-pending U.S. patent application Ser. No. 14/137,931 filed Dec. 20, 2013, which is a continuation of U.S. patent application Ser. No. 12/684,839, filed Jan. 8, 2010, now U.S. Pat. No. 8,613,753, which, in turn, is a continuation-in-part of U.S. patent application Ser. No. 11/849,225, filed Aug. 31, 2007, now U.S. Pat. No. 8,668,712; the contents of each of the foregoing are incorporated by reference herein.

FIELD OF THE INVENTION

The present invention pertains generally to the field of devices for use in the treatment of venous thrombosis. More particularly, the present invention relates to an apparatus for detecting a thrombus captured in a vena cava filter within a patient's blood vessel.

BACKGROUND

A deep vein thrombosis (DVT) is a blood clot, or thrombus, that forms in a vein. A principal risk of a DVT is that it will embolize and become a life-threatening pulmonary embolism (PE). The disease process venous thromboembolism (abbreviated as VTE or DVT/PE) can refer to DVT and/or PE. The accepted standard of care for patients with DVT is anticoagulant therapy. Inferior vena cava (IVC) filters are typically reserved for those patients who fail anticoagulant therapy, or have a complication or contraindication to anticoagulant therapy. In some cases, both anticoagulant therapy and an IVC filter may be used to treat patients with DVT.

An IVC filter is deployed in the vena cava to capture thrombotic or embolic material before it can cause a PE. The filter may be deployed permanently, or as a temporary IVC filter that may be retrieved after a period of time. A temporary IVC filter may be deployed while thrombolytic medication is administered to reduce the thrombus. The temporary IVC filter would capture any parts of the thrombus that might come loose while the thrombolytic medication is administered. After a period of time, the risk of a PE may be lessened and the filter may be retrieved.

The use of an IVC filter, particularly a temporary IVC filter, may require periodic monitoring to detect whether and to what extent thrombotic material is captured by the IVC filter. As the IVC filter captures thrombotic material, the filter may become burdened with so much thrombotic material that it forms an obstacle for blood flow to the heart. An overly burdened temporary IVC filter may also be filled with enough thrombotic material to affect the collapsibility of the filter making the filter more difficult to retrieve, increasing the risk of dislodging the thrombotic material and causing a PE. Prior to retrieval, thrombus captured in an overly-burdened filter may be treated to reduce the size of the thrombotic material. Treatment may be by chemical means, such as by administration of a thrombolytic agent, by mechanical means, such as by employing a structure that mechanically disrupts the thrombotic material, by pressure such as pressurized fluid injection or sonication of the thrombus or by thermal means, such as by laser or other energetic means for disrupting the thrombus. It will be understood that the foregoing means for treating the thrombus captured in the IVC filter are exemplary only and non-limiting. Alternative means for treating or reducing the thrombus captured within the IVC filter as may be currently or hereinafter known in the art are also contemplated by the present invention. Under all circumstances, however, prior to removing a temporary IVC filter, it is highly desirable to detect both the presence of thrombus in the filter and evaluate its size and effect on withdrawing the temporary IVC filter while controlling the risk of pulmonary embolism as a result of thrombotic material being released from the temporary IVC filter during retrieval.

Known methods of detecting the presence of a thrombus in an IVC filter rely on the use of expensive imaging processes and medical imaging equipment. When it is desired to determine if a thrombus is present in an IVC filter deployed in a patient, the patient is typically moved to an imaging facility. The area in which the filter is deployed in the patient's body is imaged. If the imaging is performed using x-rays, the imaging generates cavograms or angiograms, which are then analyzed to determine if a thrombus is present in the filter. Other such imaging methods include intravascular ultrasound ("IVUS"), venography, and CT scans.

It would be desirable to be able to determine at the patient's bedside whether a thrombus is present in the IVC filter without the need for imaging, or to make preliminary determinations of the presence of a thrombus in the IVC filter prior to imaging to quantify the presence and size of the thrombus.

SUMMARY OF THE INVENTION

In one embodiment, a thrombus detection device comprises an elongate tube comprising a tube lumen extending at a substantially constant inner diameter from a first opening at a proximal end to a distal tube portion. The distal tube portion comprises a distal portion lumen extending at an increasing inner diameter to a second opening wider than the first opening. The second opening is sufficiently wide to permit entry of a thrombus into the distal portion lumen. The device for detecting the thrombus includes a coupling at the proximal end of the elongate tube which is used to couple a pump or other means, such as a syringe, for withdrawing blood or fluid from the elongate tube.

For purposes of illustration only, the present application will refer to a syringe as the pump or other means. It is expressly intended, however, that the embodiments disclosed herein are not intended to be limited a syringe as a particular type of pump or other means to draw blood into the elongate tube. Rather, other types of pumps, such as a squeeze bulb, a piston pump, a rotary pump, a syringe pump, a vacuum pump, for example, are expressly included within the scope of the embodiments disclosed herein. When coupled to the elongate tube, the pump or syringe is used to draw blood into the distal portion lumen and through the tube lumen of the elongate tube. The presence of a thrombus is indicated by the volume of blood drawn by the pump, i.e., when less blood can be drawn than expected due to obstruction of the tube lumen by the thrombus in the distal portion lumen.

In another embodiment, the elongate tube may be deployed by inserting the tube into a sheath that guides the elongate tube to the site of interest.

In another embodiment, the elongate tube may be deployed by inserting the tube into a lumen of a single or multi-lumen catheter. The catheter may be of the type that includes an attached IVC filter and a port for the lumen that opens proximal to the IVC filter.

The elongate tube in embodiments disclosed herein may be a tube member with a flexible end member attached at the distal end of the tube member. The flexible end member may have a first opening configured to attach to the distal end of the single tubular member and a second opening wider than the first opening. In another embodiment, the elongate tube may be a single component made of a flexible material and having a first opening at the proximal end and a second opening wider than the first opening at the distal end.

In another embodiment, a device is provided for detecting a thrombus, the device comprising an elongate tube with at least one tube lumen extending at a substantially constant inner diameter from a first opening at a proximal end to a distal tube portion. The distal tube portion includes a plurality of openings in fluid communication with at least one of the tube lumens. A coupling is formed or attached at the proximal end of the elongate tube. The coupling is configured to removably couple a syringe or pump, as previously described above, to the first opening of the elongate tube. The syringe is used to draw blood into the at least one thrombus detection opening and through the tube lumen of the elongate tube. The detection of a thrombus is made by using the syringe to draw blood through the elongate tube. The presence of a thrombus is indicated when less blood can be drawn than expected due to obstruction of at least some of the plurality of openings.

Various advantages, aspects and novel features of the present invention, as well as details of an illustrated embodiment thereof, will be more fully understood from the following description and drawings. Other systems, methods and features of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

FIG. 2B is a detail view of the example of an elongate tube for detecting a thrombus shown in FIG. 2A at Detail A.

DETAILED DESCRIPTION OF THE PREFERRED EMBODIMENTS

Figure 1:
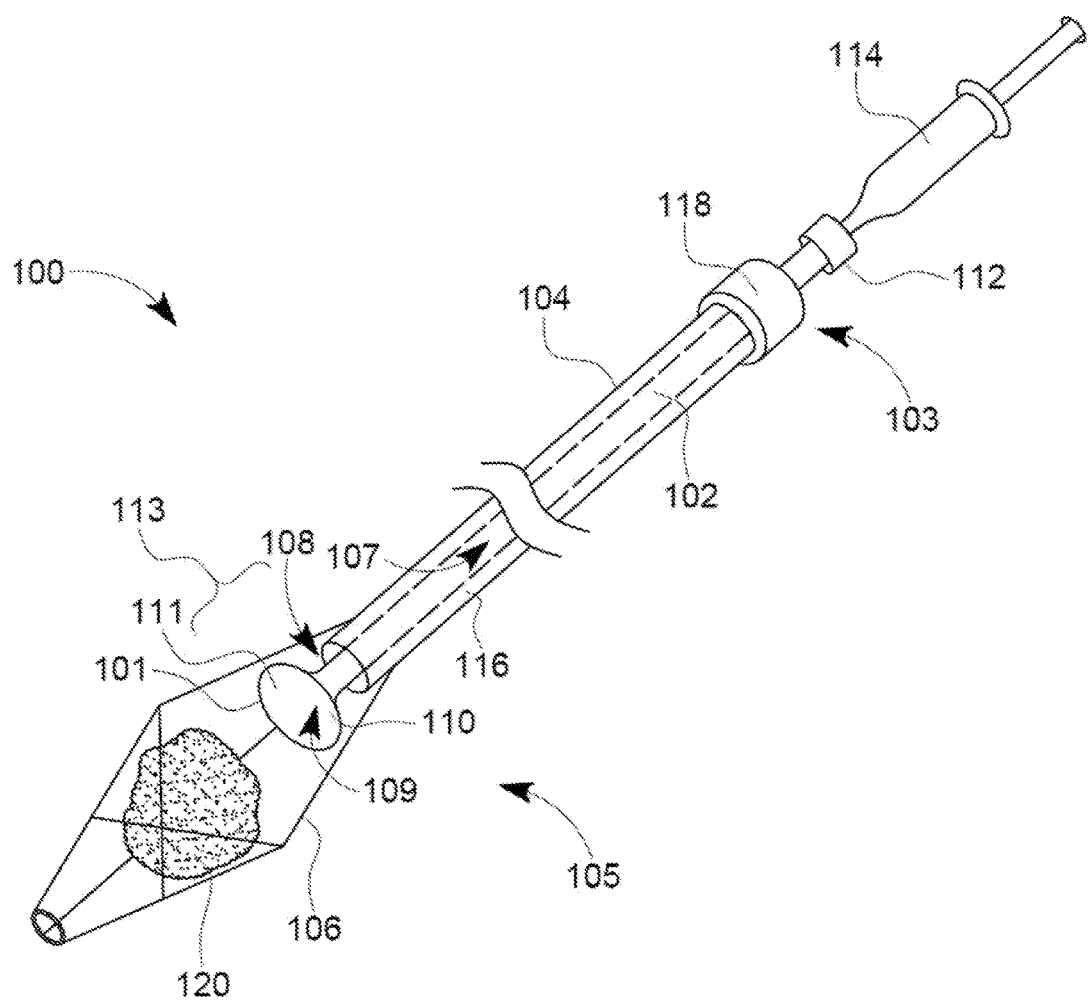
FIG. 1 is a perspective view of an example of a thrombus detection device used with a catheter having an IVC filter.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein, the term "syringe" shall refer to any device that may be used for withdrawing blood into a tube. For example, a syringe being a simple pump, any suitably configured pump may be used to aspirate blood into a tube. Such types of withdrawing devices include a wide variety of pumps, such as a squeeze bulb, a piston pump, a rotary pump, a syringe pump, a peristaltic pump or a vacuum pump.

Described below with reference to FIGS. 1-4B are examples of devices for detecting a thrombus in a patient's blood vessel. The examples of the devices for detecting a thrombus described below find particularly advantageous use in patients using an inferior vena cava filter ("IVC filter"). After the IVC filter has been deployed, the filter may become burdened with thrombi. In some instances, it may be advantageous or even necessary to break up the thrombotic material captured by the filter. It may be advantageous to determine if the filter has become burdened with thrombotic material at any time during the deployment of the filter. Typically, whether or not the filter has become burdened with thrombotic material is of most interest when the filter is to be removed. Using example implementations of devices for detecting a thrombus, the thrombotic material may be detected to determine the best way to manage the thrombotic material. The devices for detecting at thrombus advantageously permit thrombus detection at a patient's bedside without the need for expensive imaging equipment.

With reference to FIG. 1, according to one embodiment, a central venous access filter ("CVAF") 100 is composed generally of a single lumen central venous access catheter body 104 having a distal port 108 associated with a catheter lumen 116, an IVC filter 106 attached to a distal end 105 of the catheter body 104. The catheter body 100 includes a hub 118 at the proximal end 103 to provide fluid coupling with the catheter lumen 116.

The IVC filter 106 may be any suitable filtering device configured to capture embolic material of a size that is sufficient to create a risk of a pulmonary embolism if it is not filtered. In an example implementation, the IVC filter 106 may be a self-expanding structure made of a plurality of struts formed to capture a thrombus. A first plurality of struts may attach to the catheter body 102 and a second plurality of struts interconnect to provide a filtering structure.

A thrombus detection device 101 is disposed within the catheter lumen 116 of the catheter body 104 extending from the proximal end 103 to the distal end 105 of the catheter body 104. The thrombus detection device 101 is formed as an elongate tube 102 having a tube lumen 107 extending at a substantially constant inner diameter from a first opening (not shown) at a proximal end 103 to a distal tube portion 111. The distal tube portion 111 includes a resilient section 113 formed of a resilient material. The resilient section 113 of the distal tube portion 111 may have an increasing inner diameter as it extends distally from the distal portion lumen 109 to a second opening 110 that is greater than a diameter of the catheter lumen 116 at the distal end 105 of the catheter body 102. In this configuration, the resilient section 113 has a generally conical shape that opens distally relative to the longitudinal axis of the thrombus detection device 101. The second opening 110 is configured to be sufficiently wide to permit thrombus 120 captured by the IVC filter 106 to abut the resilient portion 111 and at least partially obstruct the second opening 110. It will be understood by those skilled in the art that alternative configurations of the resilient section 113 are contemplated by the embodiments disclosed herein, with the proviso that the resilient section 113 should be capable of being brought into contact with the thrombus 120 without substantial risk of lysing or otherwise disrupting the thrombus 120 and that it have a geometric configuration sufficient to engage the thrombus 120 in a manner that obstructs the second opening 110 and makes withdrawing blood through the elongate tube 102 more difficult than when the second opening 110 is not so obstructed.

The thrombus detection device 101 includes a coupling 112 at the proximal end 103 of the elongate tube 102. The coupling 112 is configured to removably couple a syringe 114 to the first opening of the elongate tube 102 where the syringe is used to draw blood into the distal portion lumen 109 and through the elongate tube 102. When the syringe 114 is coupled to the elongate tube 102, an attempt to withdraw blood may be initiated as the elongate tube 102 is advanced into the region encompassed by the IVC filter 106 and in proximity to the thrombus 120, if present in the IVC filter 106. Gradation markings (not shown) that may be provided on the elongate tube 102 serve to indicate the position of the distal portion lumen 109 relative to the filter 106. That is, that elongate tube 102 has a known length, the length of the catheter body 104 and IVC filter 106 is known, and therefore the position of the distal tube portion 111 relative to the IVC filter 106 may be known by virtue of the graduation markings. As the elongate tube 102 is advanced within the filter 106, blood is withdrawn by the syringe 114. When the distal portion lumen 109 is in proximity to, adjacent to or abutting thrombus 120, the syringe 114 draws the thrombus 120 into the distal portion lumen 109 of the elongate tube 102 and obstruct blood from entering the tube lumen 107 creating a difficulty or inability to withdraw blood into the elongate tube 102 using the syringe 114. This difficulty or inability to withdraw blood into the elongate tube 102 may then be deemed as an indication that the thrombus 120 is present in the filter 106.

The resilient section 113 of the elongate tube 102 may be of a resilient, flexible or elastic material capable of collapsing to a reduced profile when inserted into the catheter body 104. Once the wider second opening 110 extends out through the distal port 108 of the catheter body 104, the resilient section 113 diametrically expands to an enlarged profile.

The elongate tube 102, including the resilient section 113, may be made of a polymeric, metallic or combination polymeric/metallic biocompatible material. The elongate tube 102 in FIG. 1 may be constructed as a single tube having the enlarged resilient section 113 be integral with the remainder of the elongate tube 102. Alternatively, elongate tube 102 may be constructed of single tubular member and a substantially secondary resilient member connected to the distal end of the tubular member as described below with reference to FIGS. 2A-2D.

Figure 2A:
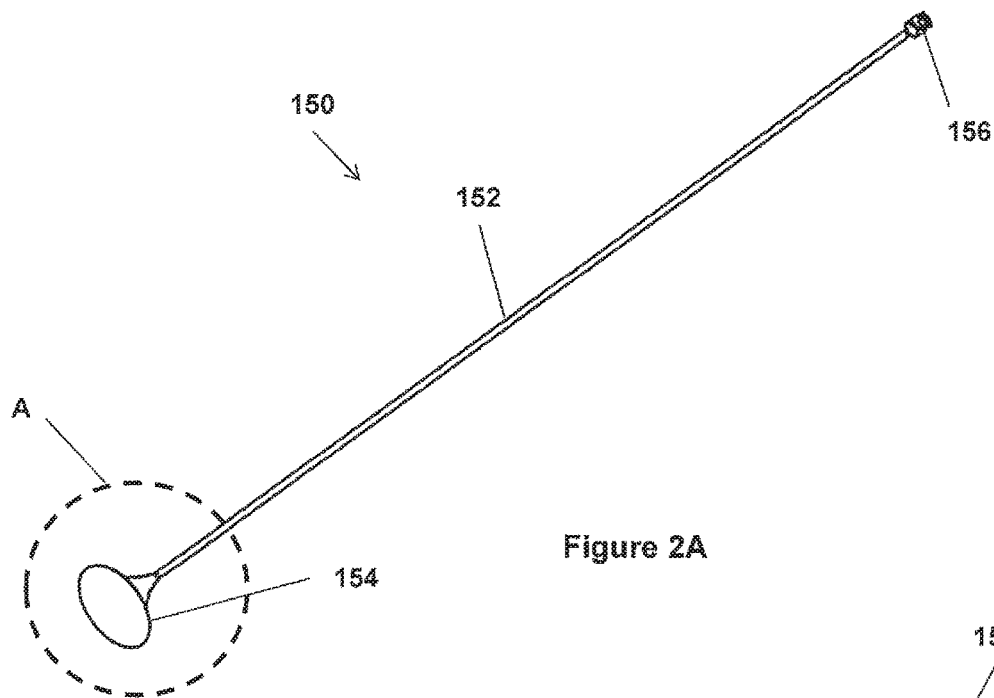
FIG. 2A is a perspective view of an example of an elongate tube for detecting a thrombus.
Figure 2C:
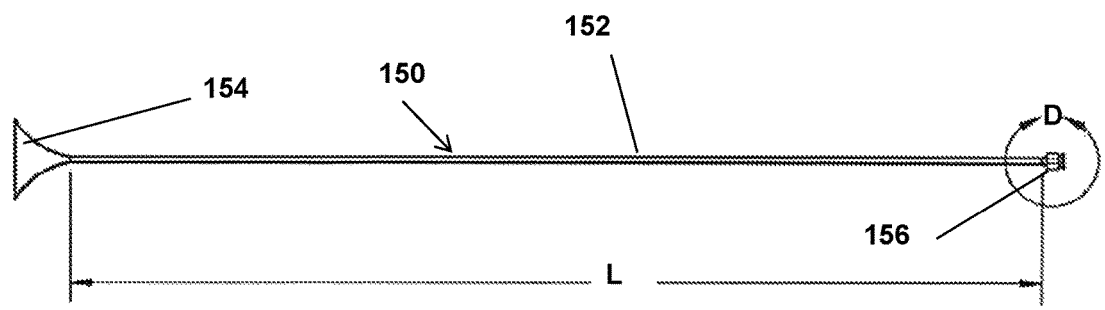
FIG. 2C is a side view of the example of an elongate tube for detecting a thrombus shown in FIG. 2A.
Figure 2D:
FIG. 2D is a detail view of the example of an elongate tube for detecting a thrombus shown in FIG. 2A at Detail D.
Figure 3A:
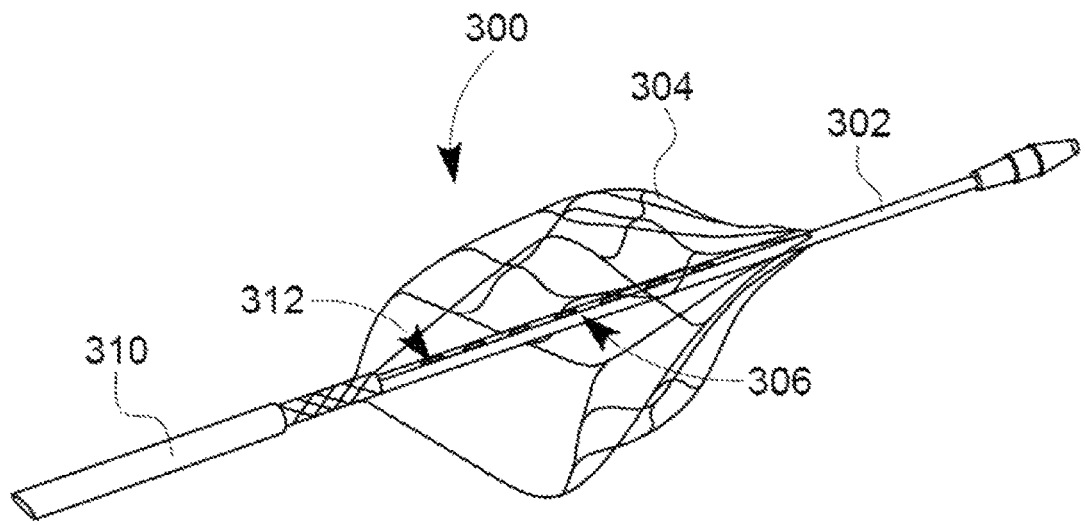
FIG. 3A is a perspective view of another example of a thrombus detection device.
Figure 3B:
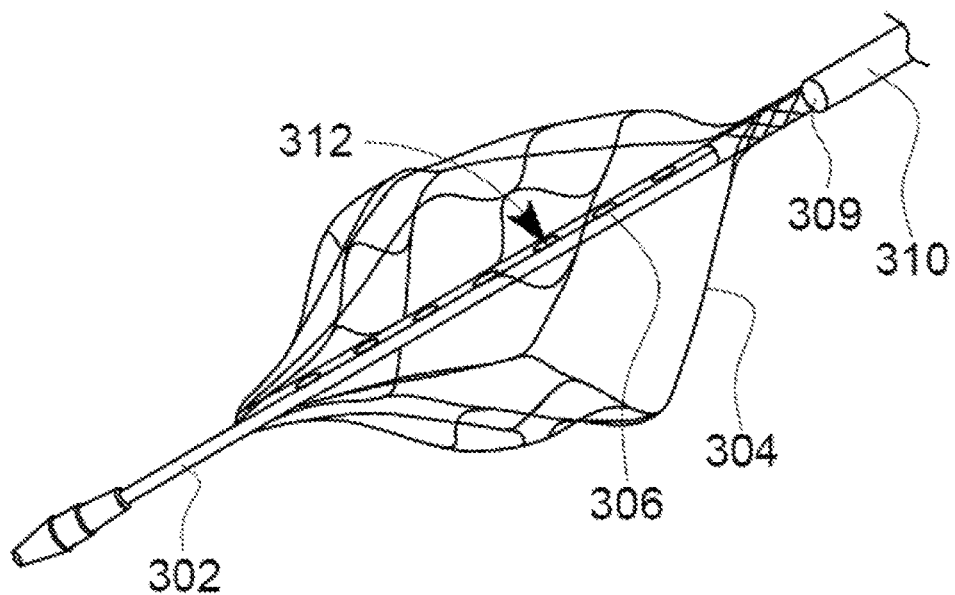
FIG. 3B is another view of the example of a thrombus detection device of FIG. 3A.

FIGS. 2A-2D illustrate different views of an example implementation of an elongate tube 150 of a type that may be used in the example shown in FIG. 1. FIG. 2A is a perspective view of the elongate tube 150. FIG. 2B is a detail view of the elongate tube shown in FIG. 2A at Detail A. FIG. 2C is a side view of the elongate tube shown in FIG. 2A. FIG. 2D is a detail view of the elongate tube shown in FIG. 2C at Detail B.

Referring to FIGS. 2A-2D, the elongate tube 150 includes a tube member 152, which forms the tube lumen 107 described above with reference to FIG. 1, and a flexible end member 154, which is the distal tube portion 111 that forms the distal portion lumen 109 described above with reference to FIG. 1. The flexible end member 154 is attached to the tube member 152 at a distal end of the tube member 152. The flexible end member 154 attaches to the elongate tube 150 at a first end member opening 155 sized to fit the opening of the elongate tube 150. The flexible end member 154 opens distally to a second end member opening 157 wider than the first end member opening 155.

The tube member 152 extends from a coupling 156 at a proximal end to the attachment to the flexible end member 154 at a distal end of the tube member 154. A tube lumen 159 extends from the opening at the proximal end to the opening at the distal end. The tube member 152 and the flexible end member 154 may be made of the same or different materials. The tube member 152 may be made of any suitable biocompatible metallic or polymeric material with sufficient flexibility to allow insertion into the tortuous routes that may be formed by body's blood vessels. The flexible end member 154 may be made of any suitable biocompatible metallic or polymeric material with sufficient flexibility to collapse when inserted through a catheter and to self-expand to its un-collapsed state when the flexible end member 154 extends out of the catheter. The tube member 152 may be of any suitable length, which typically depend on the length of the catheter used to deploy the elongate tube 150.

The coupling 156 may be a luer-lock in fluid communication with the first opening at the proximal end of the elongate tube 150, which is in fluid communication with the elongate tube lumen. However, any suitable mechanism for attaching a syringe, or any other suitable fluid withdrawing device, so as to be in fluid communication with the lumen of the elongate tube may be used.

The flexible end member 154 shown in FIGS. 2A-2D is cone shaped. However, the flexible end member 154 may be any suitable shape such that the second end member opening 157 is wider than the first end member opening 155. The shape of the flexible end member 154 should allow for a thrombus to be funneled or guided in towards the first end member opening 155 when blood is being withdrawn into the tube lumen 159. The size of the first end member opening 155 and the inner diameter of the lumen of the elongate tube 152 should be such that the smallest significantly sized thrombus would obstruct blood from flowing into the tube lumen 159 of the elongate tube 152. In another embodiment, the inner diameter of the tube lumen 159 may also be such that thrombi of a desired may pass through the tube lumen 159 along with blood being withdrawn.

The elongate tube 150 in FIGS. 2A-2D may be deployed as a thrombus detection device by inserting the elongate tube 150 into a catheter device such as the catheter device 100 described above with reference to FIG. 1. In one embodiment, the elongate tube 150 includes a length L, as shown in FIG. 2C. The catheter device 100 shown in FIG. 1 is a single lumen device. However, any single or multi-lumen catheter device may be used as well. For example, multi-lumen catheter devices such as those described in U.S. Pat. No. 8,613,753, which is incorporated herein in its entirety, incorporate multiple lumens, at least one of which may be configured for deployment of examples of the devices for detecting a thrombus described herein. One advantage of using a multi-lumen catheter device is that a lumen may be configured for thrombus detection and at least one other lumen may be used for infusion of thrombolytic agents, which may be dispensed when a thrombus is detected. The thrombus detection lumen may be configured by providing an opening to the thrombus detection lumen at a location of the catheter that would put the wide opening of the elongate tube near any thrombi captured in the filter. A hub on the catheter device may be configured to provide an opening through which the elongate tube may be inserted into the thrombus detection lumen.

In an embodiment in which a single lumen catheter such as the catheter 100 shown in FIG. 1 is used, the single lumen may be used for deployment of the thrombus detection device as described above. When a thrombus is detected, thrombolytic agents may be injected into the lumen of the thrombus detection device. The agents exit through the wide opening of the elongate tube, which is advantageously near the thrombus that is the target of the thrombolytic agents.

In another example implementation, the thrombus detection device may be deployed using a simple sheath that may be inserted into the patient's blood vessel. The distal end of the sheath may be placed near a desired location. The desired location may be proximal to an existing filter that may or may not be attached to a catheter body. The sheath may also be a sheath that already contains a catheter that may or may not include an attached filter device so that the sheath contains both the catheter device and the thrombus detection device.

In alternative embodiments, the thrombus detection device need not incorporate a flexible end member with a wide opening for guiding a thrombus towards the opening to the lumen of the elongate tube. Referring to FIGS. 3A-4B, a thrombus detection device 300 includes a catheter having a tip portion 302, a thrombus detection portion 306 and an elongate tube portion 309 integrated as a single catheter member.

The thrombus detection portion 306 is disposed between the tip portion 302 and the elongate tube portion 309 within a region encompassed by an attached IVC filter 304. The thrombus detection portion 306 includes a plurality of openings 312 extending longitudinally along the thrombus detection portion 306. The plurality of openings 312 pass through a wall surface of the thrombus detection portion 306 of the catheter and are in fluid communication with at least one tube lumen formed in the elongate tube portion 309 and the thrombus detection portion 306 of the catheter. The openings 312 may be equally or unequally spaced along the thrombus detection portion 306 and may be positioned at any position about the circumference of the thrombus detection portion 306 of the catheter. The plurality of openings 312 may also comprise a first plurality of openings 312 on one side of the thrombus detection portion 306 and another plurality of openings on the other side of the thrombus detection portion 306.

The attached IVC filter 304 may be any suitable filtering device configured to capture embolic material of a size that is sufficient to create a risk of a pulmonary embolism if it is not filtered. In an example implementation, the IVC filter 304 may be a self-expanding structure made of a plurality of struts formed to capture a thrombus. A first plurality of struts may attach to the catheter body at the distal end of the elongate tube portion 309, and a second plurality of struts interconnect to provide a filtering structure. The IVC filter 304 may be a collapsible self-expanding filter structure that collapses when the thrombus detection portion 306 of the catheter is inserted into a sheath 310, and self-expands when the thrombus detection portion 306 of the catheter extends beyond the distal end of the sheath 310.

The thrombus detection portion 306 of the catheter body is disposed in a region of the catheter body bounded by the IVC filter 304. The openings 312 are in fluid communication with the tube lumen extending through the elongate tube portion 309 of the catheter. The proximal end of the catheter may include a coupling as described above with reference to the embodiments of FIGS. 1-2D. A syringe coupled to the coupling may be used to withdraw blood through the openings 312 and the tube lumen of the elongate tube portion 309 of the catheter.

The IVC filter 304 may be deployed and left in a patient's blood vessel for a prescribed amount of time. While the IVC filter 304 is operating in the patient's blood vessel, the IVC filter 304 may be checked to determine if it is burdened by a thrombus. Typically, the IVC filter 304 is checked prior to its removal. In order to check for a thrombus in the IVC filter 304, a syringe is coupled to the coupling at the proximal end of the catheter. The syringe is then used in an attempt to draw blood into the openings 312 and the elongate tube portion 309 of the catheter. If the IVC filter 304 does not contain any thrombi, the blood will be easily drawn into the openings 312. If the IVC filter 304 contains a thrombus of sufficient size to obstruct the openings, the blood will be obstructed from entry into the openings 312 when an attempt is made to aspirate the blood into the openings 312. As the size of the thrombus increases, the number of obstructed openings 312 increases creating a greater obstruction of blood into the openings 312 and an increase in difficulty withdrawing blood. The relative increase in the difficulty of withdrawing blood provides an indication of the size of the mass of thrombotic material burdening the IVC filter 304.

Figure 4A:
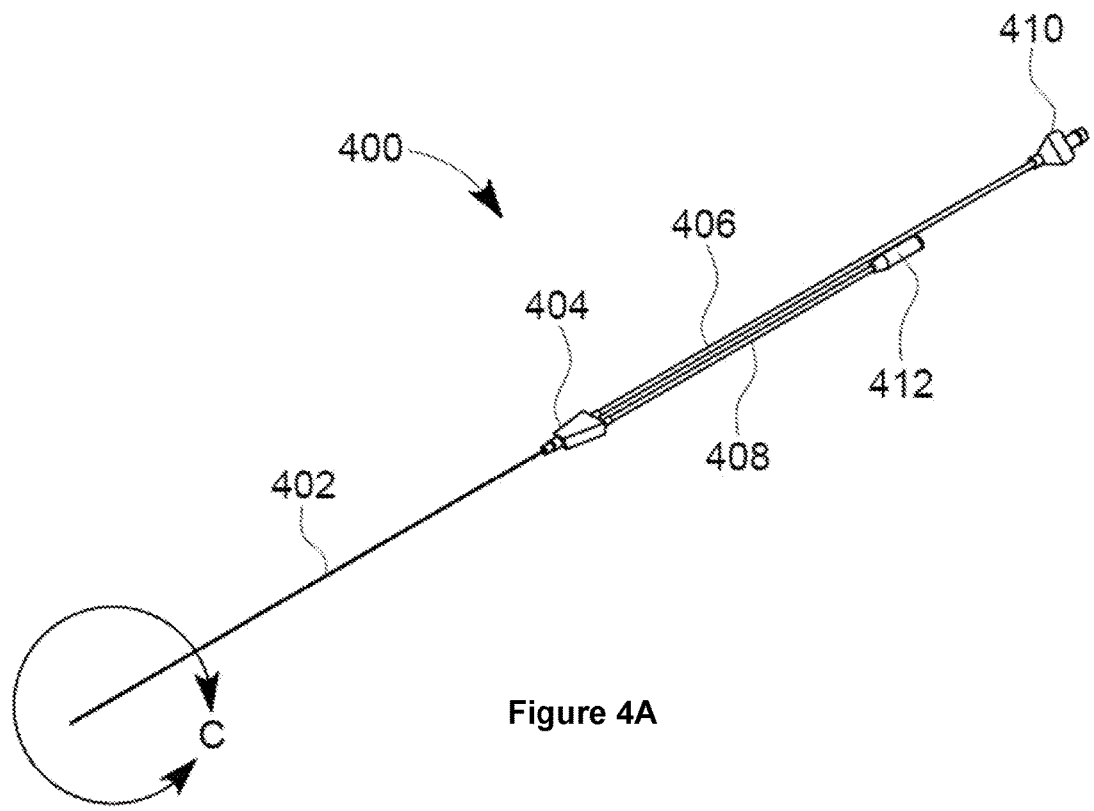
FIG. 4A is a perspective view of another example of a thrombus detection device.
Figure 4B:
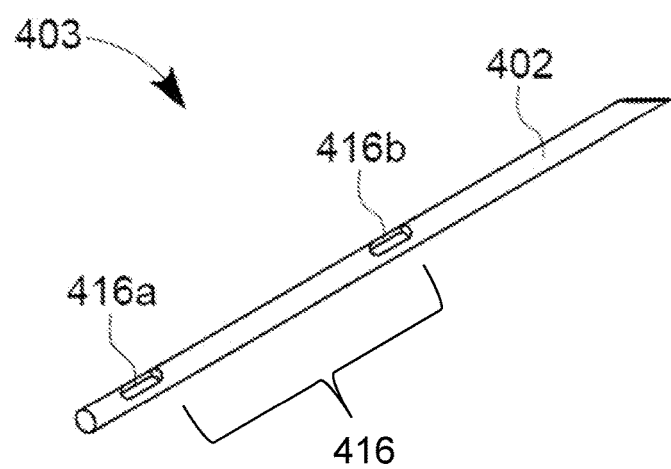
FIG. 4B is a detail view of the example of a thrombus detection device of FIG. 4A at Detail C.

FIGS. 4A and 4B show another embodiment of a thrombus detection device 400. FIG. 4A is a perspective view of the thrombus detection device 400. FIG. 4B is a detail view of the thrombus detection device 400 at Detail C in FIG. 4A. The thrombus detection device 400 in FIGS. 4A and 4B includes an elongate tube 402, a hub 404, a first syringe line 406 having a first coupling 410, and a second syringe line 408 having a second coupling 412. The elongate tube 402 includes a distal tube portion 403 comprising a plurality of openings 416. The example elongate tube 402 shown in FIG. 4B includes a first thrombus detection opening 416a close to the tip and a substantially aligned second thrombus detection opening 416b a distance away from the first thrombus detection opening 416a. Additional openings 416 may be provided further proximally along the elongate tube 402. Additional openings 416 may also be provided diametrically opposite the first and second openings 416a and 416b.

The elongate tube 402 may include a first lumen in fluid communication with a first plurality of openings and a second lumen in fluid communication with a second plurality of openings. The first plurality of thrombus openings may be distributed on one side of the distal tube portion 403 and the second plurality of openings on the other side of the distal tube portion 403. The hub 404 provides fluid pathways so that the first lumen is in fluid communication with the first syringe line 406 and the second lumen is in fluid communication with the second syringe line 408. As described above with reference to FIGS. 3A and 3B, the openings 416 may be spaced so as to quantify the size of the clot that may be obstructing the blood withdrawal. By attempting to withdraw blood via lumens in fluid communication with openings on opposite sides of the distal tube portion 403, one can determine whether one side of the IVC filter is more burdened than the other side. The indication of the size of the clots and of the distribution of the thrombotic material in the IVC filter provides information that may be used to determine how best to manage the clots.

Example embodiments of devices for detecting a thrombus are described above with reference to FIGS. 1-4B. The examples described with reference to FIGS. 1-2D use an elongate tube having a single lumen that opens to a distal tube portion with a lumen having an inner diameter that increases to a wide opening. Thrombus detection is achieved when attempting to draw blood. The presence of a thrombus in the distal tube portion lumen obstructs blood from flowing into the elongate tube. The examples described with reference to FIGS. 3A-4B use an elongate tube having either a single lumen or multiple lumens in fluid communication with openings at the distal end of the elongate tube.

A method to detect a thrombus within a blood vessel may be performed using any suitable example of the above described devices for detecting a thrombus. The method comprises the steps of:
a. introducing an elongate tube having at least one opening in a distal end of the elongate tube into the blood vessel.
b. positioning the distal end of the elongate tube at a site of interest;
c. attaching a syringe to a coupling at a proximal end of the elongate tube; and
d. using the syringe to withdraw blood through the elongate tube where a thrombus in the at least one opening of the flexible member obstructs the blood withdrawal indicating the presence of the thrombus.

The site of interest indicated in step a may be the region encompassed by a filter. The distal end of the elongate tube may be brought to the region encompassed by the IVC filter through a lumen of a catheter or a sheath extending in the patient's blood vessels to the region encompassed by the IVC filter. The filter may or may not be attached to a distal end of a catheter. The method may thus include the steps of:
a. inserting a sheath into the blood vessel; and
b. inserting the elongate tube to the blood vessel through the sheath.

Alternatively, the method may include the steps of:
a. inserting a catheter body having a lumen with a distal port on a distal end of the catheter body and a proximal port on a proximal end of the catheter body into the blood vessel; and
b. inserting the elongate tube into the proximal port of the catheter body until the distal end of the elongate tube exits the distal port.

In one embodiment, a device for detecting the presence of a thrombus in a patient's blood vessel is disclosed and comprises: an elongate tube comprising a tube lumen extending at a substantially constant inner diameter from a proximal end opening at a proximal end to a distal tube portion comprising a plurality of openings in fluid communication with the tube lumen; and a coupling attached at the proximal end opening of the elongate tube, the coupling configured to configured to removably couple a syringe to the first opening of the elongate tube where the syringe is used to draw blood through the plurality of openings and through the tube lumen of the elongate tube; wherein detection of a thrombus is determined by drawing blood through the openings and through the elongate tube, and indicating the presence of a thrombus when less blood can be drawn than expected due to obstruction of at least some of the plurality of openings. The coupling is a luer-lock. The elongate tube is made of a polymeric material, a metallic material, or a combination thereof. The plurality of openings extend longitudinally along the distal portion of the elongate tube. The plurality of openings includes a first plurality of openings extending along one side of the elongate tube and a second plurality of openings extending along an opposite side of the elongate tube. The tube lumen of the elongate tube is a first lumen, the tube lumen comprises a second lumen, the proximal end opening is a first proximal end opening in fluid communication with the first lumen, the elongate tube comprises a second proximal end opening in fluid communication with the second lumen; the first plurality of openings is in fluid communication with the first lumen; and the second plurality of openings is in fluid communication with the second lumen. Each of the plurality of openings are spaced at equal distances longitudinally along the distal tube portion of the elongate tube, and where the equal distances provide an indication of clot size when multiple openings may be obstructed as the size of the thrombus increases.

Thus there have been described examples of a thrombus detection device which include, generally, an elongate tube extending from a first opening at a proximal end to an at least one opening at a distal end. A coupling is formed at the first opening to permit attachment of a syringe that may be used to withdraw blood through the elongate tube. These and other aspects of the present invention are provided by way of non-limiting examples, with the claims appended hereto serving to define the scope of the subject matter regarded as the invention.

What is claimed is:

1. A medical device comprising:
   a. a catheter body having a distal port positioned in a distal portion of the catheter body, the distal port being in fluid association with a catheter lumen extending to a proximal port in a proximal portion of the catheter body;
   b. an IVC filter coupled to the distal portion of the catheter body and positioned such that the distal port opens at a proximal side of the IVC filter;
   c. an elongate tube disposed and reciprocally moveable within the catheter lumen, the elongate tube comprising a tube lumen extending at a substantially constant inner diameter from a first opening at a proximal end to a distal tube portion comprising a distal portion lumen extending at an increasing inner diameter to a second opening wider than the first opening, the second opening being sufficiently wide to permit entry of a thrombus into the distal portion lumen, where the distal tube portion is configured to diametrically collapse for insertion into the catheter lumen at the proximal port and to diametrically expand when the elongate tube is in an extended position and the distal tube portion projects out of the catheter lumen at the distal port; and
   d. a coupling in fluid communication with the first opening of the proximal end of the elongate tube, the coupling configured to removably couple a syringe to the first opening of the elongate tube where the syringe is capable of drawing blood into the distal portion lumen and through the tube lumen of the elongate tube.

2. The medical device of claim 1, where the elongate tube comprises:
   a. a tube member forming the tube lumen in a proximal tube portion of the elongate tube, the tube member extending from the proximal end of the elongate tube to a distal tube member opening of substantially the same size as the first opening of the elongate tube;
   b. a flexible end member forming the distal tube portion of the elongate tube, the flexible end member having a first end member opening configured to attach to the distal tube member opening, the flexible end member extending distally to form the distal portion lumen.

3. The medical device of claim 2, where the elongate tube is formed as a single tubular member and where the coupling is a luer-lock.

4. The medical device of claim 3, where the flexible end member is made of a polymeric material, a metallic material, or a combination thereof, and where the single tubular member forming the elongate tube is made of a polymeric material, a metallic material, or a combination thereof.

5. The medical device of claim 3, where the flexible end member is in a generally conical shape between the first flexible member opening to the second opening wider than the first opening.

6. The medical device of claim 4, where a distal end of the single tubular member is formed in a generally conical shape.

* * * * *